(12) United States Patent
Macoviak et al.

(10) Patent No.: US 7,381,220 B2
(45) Date of Patent: Jun. 3, 2008

(54) DEVICES, SYSTEMS, AND METHODS FOR SUPPLEMENTING, REPAIRING, OR REPLACING A NATIVE HEART VALVE LEAFLET

(75) Inventors: John A. Macoviak, La Jolla, CA (US); Robert T. Chang, Belmont, CA (US); David A. Rahdert, San Francisco, CA (US); Timothy R. Machold, Moss Beach, CA (US); Rick A. Soss, Burlingame, CA (US)

(73) Assignee: Ample Medical, Inc., Foster City, CA (US)

( * ) Notice: Subject to any disclaimer, the term of this patent is extended or adjusted under 35 U.S.C. 154(b) by 422 days.

(21) Appl. No.: 10/676,815

(22) Filed: Oct. 1, 2003

(65) Prior Publication Data

US 2005/0010287 A1 Jan. 13, 2005
US 2005/0267573 A9 Dec. 1, 2005

Related U.S. Application Data

(63) Continuation-in-part of application No. 09/666,617, filed on Sep. 20, 2000, now Pat. No. 6,893,459, and a continuation-in-part of application No. PCT/US02/31376, filed on Oct. 1, 2002.

(60) Provisional application No. 60/429,462, filed on Nov. 26, 2002, provisional application No. 60/429,709, filed on Nov. 26, 2002, provisional application No. 60/429,444, filed on Nov. 26, 2002, provisional application No. 60/326,590, filed on Oct. 1, 2001.

(51) Int. Cl.
*A61F 2/24* (2006.01)

(52) U.S. Cl. .................................... 623/2.12

(58) Field of Classification Search ............... 623/1.24, 623/1.26, 2.14, 2.18, 2.12, 2.36, 2.37, 2.38
See application file for complete search history.

(56) References Cited

U.S. PATENT DOCUMENTS

| | | | |
|---|---|---|---|
| 4,056,854 A | 11/1977 | Boretos et al. |
| 4,275,469 A | 6/1981 | Gabbay |
| 4,994,069 A | 2/1991 | Ritchart et al. |
| 5,360,444 A | 11/1994 | Kusuhara |
| 5,370,685 A | 12/1994 | Stevens |
| 5,545,241 A | 8/1996 | Vanderauwera et al. |

(Continued)

OTHER PUBLICATIONS

Templeton III, et al. "Experimental Reconstruction of Cardiac Valves by Venous and Pericardial Grafts." Annals of Surgery vol. 129, No. 2, Feb. 1949, 161-176.

(Continued)

*Primary Examiner*—Alvin J. Stewart
(74) *Attorney, Agent, or Firm*—Ryan Kromholz & Manion, S.C.

(57) ABSTRACT

Devices, systems and methods supplement, repair, or replace a native heart valve. The devices, systems, and methods employ an implant that, in use, extends adjacent a valve annulus. The implant includes a mobile neoleaflet element that occupies the space of at least a portion of one native valve leaflet. The implant mimics the one-way valve function of a native leaflet, to resist or prevent retrograde flow. The implant restores normal coaptation of the leaflets to resist retrograde flow, thereby resisting eversion and/or prolapse, which, in turn, reduces regurgitation.

4 Claims, 9 Drawing Sheets

U.S. PATENT DOCUMENTS

| | | |
|---|---|---|
| 5,716,397 A | 2/1998 | Myers |
| 5,776,189 A | 7/1998 | Khalid |
| 5,792,155 A | 8/1998 | Van Cleef |
| 5,830,224 A | 11/1998 | Cohn et al. |
| 5,855,601 A | 1/1999 | Bessler et al. |
| 5,961,440 A | 10/1999 | Schweich, Jr. et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,077,214 A | 6/2000 | Mortier et al. |
| 6,099,542 A | 8/2000 | Cohn et al. |
| 6,102,932 A | 8/2000 | Kurz |
| 6,162,168 A | 12/2000 | Schweich, Jr. et al. |
| 6,165,119 A | 12/2000 | Schweich, Jr. et al. |
| 6,183,411 B1 | 2/2001 | Mortier et al. |
| 6,210,432 B1 | 4/2001 | Solem et al. |
| 6,260,552 B1 | 7/2001 | Mortier et al. |
| 6,261,222 B1 | 7/2001 | Schweich, Jr. et al. |
| 6,287,339 B1 | 9/2001 | Vazquez et al. |
| 6,299,637 B1 * | 10/2001 | Shaolian et al. ............ 623/1.24 |
| 6,312,464 B1 | 11/2001 | Navia |
| 6,312,465 B1 | 11/2001 | Griffin et al. |
| 6,332,864 B1 | 12/2001 | Schweich, Jr. et al. |
| 6,332,893 B1 | 12/2001 | Mortier et al. |
| 6,338,735 B1 | 1/2002 | Stevens |
| 6,338,740 B1 | 1/2002 | Carpentier |
| 6,402,781 B1 | 6/2002 | Langberg et al. |
| 6,419,695 B1 | 7/2002 | Gabbay |
| 6,419,696 B1 | 7/2002 | Ortiz et al. |
| 6,440,164 B1 | 8/2002 | DiMatteo et al. |
| 6,454,799 B1 | 9/2002 | Schreck |
| 6,458,153 B1 * | 10/2002 | Bailey et al. ............... 623/1.24 |
| 6,503,272 B2 * | 1/2003 | Duerig et al. ............... 623/1.24 |
| 6,514,194 B2 | 2/2003 | Schweich, Jr. et al. |
| 6,537,198 B1 | 3/2003 | Vidlund et al. |
| 6,589,160 B2 | 7/2003 | Schweich, Jr. et al. |
| 6,616,684 B1 | 9/2003 | Vidlund et al. |
| 6,626,899 B2 | 9/2003 | Houser et al. |
| 6,629,534 B1 | 10/2003 | St. Goar et al. |
| 6,656,221 B2 | 12/2003 | Taylor et al. |
| 6,669,709 B1 | 12/2003 | Cohn et al. |
| 6,676,699 B2 * | 1/2004 | Shiu .......................... 623/1.24 |
| 6,685,739 B2 * | 2/2004 | DiMatteo et al. ........... 623/1.24 |
| 6,702,826 B2 | 3/2004 | Liddicoat et al. |
| 6,709,456 B2 | 3/2004 | Langberg et al. |
| 6,723,038 B1 | 4/2004 | Schroeder et al. |
| 6,764,510 B2 | 7/2004 | Vidlund et al. |
| 6,793,618 B2 | 9/2004 | Schweich, Jr. et al. |
| 6,821,297 B2 | 11/2004 | Snyders |
| 6,893,459 B1 | 5/2005 | Macoviak |
| 6,913,608 B2 | 7/2005 | Liddicoat et al. |
| 6,945,978 B1 | 9/2005 | Hyde |
| 7,004,176 B2 | 2/2006 | Lau |
| 7,070,618 B2 | 7/2006 | Streeter |
| 7,166,126 B2 | 1/2007 | Spence et al. |
| 2001/0010017 A1 | 7/2001 | Letac et al. |
| 2001/0021872 A1 | 9/2001 | Bailey et al. |
| 2001/0051824 A1 | 12/2001 | Hopkins et al. |
| 2002/0032481 A1 | 3/2002 | Gabbay |
| 2002/0065554 A1 | 5/2002 | Streeter |
| 2002/0094573 A1 | 7/2002 | Bell |
| 2002/0123802 A1 | 9/2002 | Snyders |
| 2002/0129820 A1 | 9/2002 | Ryan et al. |
| 2002/0138138 A1 | 9/2002 | Yang |
| 2003/0014104 A1 * | 1/2003 | Cribier ...................... 623/2.11 |
| 2003/0040792 A1 | 2/2003 | Gabbay |
| 2003/0120340 A1 | 6/2003 | Liska et al. |
| 2003/0233022 A1 | 12/2003 | Vidlund et al. |
| 2004/0148019 A1 | 7/2004 | Vidlund et al. |
| 2006/0241745 A1 | 10/2006 | Solem |

OTHER PUBLICATIONS

Moore et al. "Unsuitability of Transventricular Autogenous Slings For Diminishing Valvular Insufficiency." Surgery, vol. 33, No. 2, Feb. 1953, 173-182.

Murray et al. "Reconstruction of the Valves of the Heart." The Canadian Medical Association Journal, vol. 38, No. 4, Apr. 1938, 317-319.

Bolling et al. "Early Outcome of Mitral Valve Reconstruction in Patients With End-Stage Cardiomyopathy." J Thorac Cardiovasc Surg 1995; 109:676-683.

Kameda et al. "Annuloplasty For Severe Mitral Regurgitation Due to Dilated Cardiomyopathy." Ann Thorac Surg 1996; 61:1829-1832.

Bolling et al. "Intermediate-Term Outcome of Mitral Reconstruction in Cardiomyopathy." Journal of Thoracic Cardiovascular Surgery, vol. 115, No. 2, Feb. 1998, 381-388.

Harlan et al. Manual of Cardiac Surgery, vol. 2, 1981 Figs. 16.3-16.4.

Edmunds, Jr. et al. "Septal Defect." Atlas of Cardiothoracic Surgery 1990.

Koniaris, MD et al. "Dynamic Retention: A Technique for Closure of the Complex Abdomen in Critically Ill Patients." Archives of Surgery, vol. 136, No. 12, Dec. 2001, 1359-1362.

Fucci et al. "Improved Results With Mitral Valve Repair Using New Surgical Techniques." European Journal of Cardio-Thoracic Surgery, vol. 9, 1995, 621-626.

Davila et al. "Circumferential Suture of the Mitral Ring: A Method For The Surgical Correction of Mitral Insufficiency." Journal of Thoracic Surgery Nov. 1955; 30(5): 531-60.

Harken et al. "The Surgical Correction of Mitral Insufficiency" Journal of Thoracic Surgery. Dec. 1954; 28(6):604-24.

Kuykendall et al. "Surgical Correction of Chronic Mitral Insufficiency in Dogs." Surgery. Oct. 1958; 44(4):718-25.

Harken et al. "The Surgical Correction of Mitral Insufficiency." Surgical Forum 4:4-7 1953.

Davila et al. "A Method For The Surgical Correction of Mitral Insufficiency." Surgery, Gynecology and Obstetrics Apr. 1954; 98(4):407-12.

Davila et al. "The Clinical and Physiologic Criteria For Surgical Correction of Mitral Insufficiency." Journal of Thoracic Surgery Feb. 1958; 35(2):206-31.

Glover et al. "The Treatment of Mitral Insufficiency by the Purse-String Technique." Journal of Thoracic Surgery Jan. 1957; 33(1): 75-101.

Rankin et al. "A Clinical Comparison of Mitral Valve Repair Versus Valve Replacement in Ischemic Mitral Regurgitation." J Thorac Cardiovasc Surg. Feb. 1988; 95(2):165-77.

Barnard et al. "A Surgical Approach to Mitral Insufficiency." Br J Surg. May 1961; 48:655-62.

McKenzie et al. "Current Concepts in Surgical Correction of Acquired Mitral Insufficiency." Circulation. Oct. 1963; 28:603-16.

Saab et al. "Left Ventricular Aneurysm: A New Surgical Approach." Thorac Cardiovasc Surg. Feb. 1989; 37(1):11-9.

Cicek et al. "Left Ventricular Endoaneurysmorrhaphy: Effect on Left Ventricular Size, Shape and Function." Cardiology. Jul.-Aug. 1997; 88(4):340-5.

Liedtke et al. "Functional Reductions in Left Ventricular Volume." J Thorac Cardiovasc Surg. Feb. 1976; 71(2):195-206.

Sosa et al. "Recurrent Ventricular Tachycardia Associated With Postinfarction Aneurysm. Results of Left Ventricular Reconstruction." J Thorac Cardiovasc Surg. May 1992; 103(5);855-60.

Cooley, "Repair of Postinfarction Ventricular Septal Defect." J Card Surg. Jul. 1994; 9(4):427-9.

Jatene, "Left Ventricular Aneurysmectomy. Resection or Reconstruction." J Thorqc Cardiovasc Surg 1985; 89:321-31.

de Silva et al. "Postinfarction Ventricular Septal Defect. An Efficacious Technique for Early Surgical Repair." J Throac Cardiovasc Surg. Jan. 1989; 97(1):86-9.

Tashiro et al. "Extended Endocardial Repair of Postinfarction Ventricular Septal Rupture: New Operative Technique-Modification of the Komeda-David Operation." J Card Surg. Mar. 1994; 9(2):97-102.

Daggett, "Surgical Technique for Early Repair of Posterior Ventricular Septal Rupture." J Thorac Cardiovasc Surg. Aug. 1982;84(2):306-12.

Daggett et al. "Surgery for Post-Myorcardial Infarct Ventricular Septal Defect." Ann Surg. Sep. 1977;186(3):260-71.

Dor, "Left Ventricular Aneurysms: the Endoventricular Circular Patch Plasty." Semin Thorac Cardiovasc Surg. Apr. 1997;9(2):123-30.

Antunes, "Submitral Left Ventricular Aneurysms. Correction by a New Transatrial Approach." J Thorac Cardiovasc Surg. Aug. 1987;94(2):241-5.

Alvarez et al. "Technical Improvements in the Repair of Acute Postinfarction Ventricular Septal Rupture." J Card Surg. Sep. 1992;7(3):198-202.

Cox, "Surgical Management of Left Ventricular Aneurysms: A Clarification of the Similarities and Differences Between the Jatene and Dor Techniques." Semin Thorqc Cardiovasc Surg. Apr. 1997;9(2):131-8.

Skillington et al. "Surgical Treatment for Infarct-Related Ventricular Septal Defects. Improved Early Results Combined with Analysis of Late Functional Status." J thorac Cardiovasc Surg. May 1990;99(5):798-808.

Salati et al. "Severe Diastolic Dysfunction After Endoventriculoplasty." J Thorac Cardiovasc Surg. Apr. 1995;109(4):694-701.

Yacoub et al. "Anatomic Correction of the Syndrome of Prolapsing Right Coronary Aortic Cusp, Dilatation of the Sinus of Valsalva, and Ventricular Septal Defect." J thorac Cardiovasc Surg. Feb. 1997;113(2):253-60.

Wilson, W.C., "Studies in Experimental Mitral Obstruction in Relation to the Surgical Treatment of Mitral Stenosis." The British Journal of Surgery, vol. XVIII, No. 70 ;259-74.

Bailey, et al. "Surgical Repair of Mitral Insufficiency." Diseases of the Chest, vol. XIX, No. 2, Feb. 1951, 125-137.

Henderson, et al., "The Surgical Treatment of Mitral Insufficiency." Experimental Use of Transplanted Pericardium in Dogs. Surgery 33(6):858-868; 1953.

Sakakibara, "A Surgical Approach to the Correction of Mitral Insufficiency." Annals of Surgery. vol. 142, No. 2, Aug. 1955, 196-203.

Harken et al. "The Surgical Correction of Mitral Insufficiency." The Journal of Thoracic Surgery. 28(6):604-627., 1954.

Bailey et al. "The Surgical Correction of Mitral Insufficiency by the Use of Pericardial Grafts." The Journal of Thoracic Surgery, vol. 28, No. 6, Dec. 1954, 551-603.

Kay et al. "Surgical Treatment of Mitral Insufficiency." Surgery. vol. 37, No. 5. May 1955, 697-706.

\* cited by examiner

DEVICES, SYSTEMS, AND METHODS FOR SUPPLEMENTING, REPAIRING, OR REPLACING A NATIVE HEART VALVE LEAFLET

RELATED APPLICATIONS

This application is a continuation-in-part of U.S. patent application Ser. No. 09/666,617, filed Sep. 20, 2000, now U.S. Pat. No. 6,893,459, and entitled "Heart Valve Annulus Device and Methods of Using Same," which is incorporated herein by reference. This application is also a continuation-in-part of Patent Cooperation Treaty Application Ser. No. PCT/US 02/31376, filed Oct. 1, 2002 and entitled "Systems and Devices for Heart Valve Treatments," which claimed the benefit of U.S. Provisional Patent Application Ser. No. 60/326,590, filed Oct. 1, 2001, which are incorporated herein by reference. This application also claims the benefit of U.S. Provisional Application Ser. No. 60/429,444, filed Nov. 26, 2002, and entitled "Heart Valve Remodeling Devices;" U.S. Provisional Patent Application Ser. No. 60/429,709, filed Nov. 26, 2002, and entitled "Neo-Leaflet Medical Devices;" and U.S. Provisional Patent Application Ser. No. 60/429,462, filed Nov. 26, 2002, and entitled "Heart Valve Leaflet Retaining Devices," which are each incorporated herein by reference.

FIELD OF THE INVENTION

The invention is directed to devices, systems, and methods for improving the function of a heart valve, e.g., in the treatment of mitral valve regurgitation.

BACKGROUND OF THE INVENTION

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling)(see FIG. 2), the aortic and pulmonary valves are closed to prevent back flow from the arteries into the ventricles. Shortly thereafter, the tricuspid and mitral valves open (as FIG. 2 shows), to allow flow from the atria into the corresponding ventricles. Shortly after ventricular systole (i.e., ventricular emptying) begins, the tricuspid and mitral valves close (see FIG. 3)—to prevent back flow from the ventricles into the corresponding atria—and the aortic and pulmonary valves open—to permit discharge of blood into the arteries from the corresponding ventricles.

The opening and closing of heart valves occur primarily as a result of pressure differences. For example, the opening and closing of the mitral valve occurs as a result of the pressure differences between the left atrium and the left ventricle. During ventricular diastole, when ventricles are relaxed, the venous return of blood from the pulmonary veins into the left atrium causes the pressure in the atrium to exceed that in the ventricle. As a result, the mitral valve opens, allowing blood to enter the ventricle. As the ventricle contracts during ventricular systole, the intraventricular pressure rises above the pressure in the atrium and pushes the mitral valve shut.

FIG. 4 shows a posterior oblique cutaway view of a healthy human heart 100. Two of the four heart chambers are shown, the left atrium 170, and the left ventricle 140 (not shown are the right atrium and right ventricle). The left atrium 170 fills with blood from the pulmonary veins. The blood then passes through the mitral valve (also known as the bicuspid valve, and more generally known as an atrio-ventricular valve) during ventricular diastole and into the left ventricle 140. During ventricular systole, the blood is then ejected out of the left ventricle 140 through the aortic valve 150 and into the aorta 160. At this time, the mitral valve should be shut so that blood is not regurgitated back into the left atrium.

The mitral valve consists of two leaflets, an anterior leaflet 110, and a posterior leaflet 115, attached to chordae tendineae 120 (or chords), which in turn are connected to papillary muscles 130 within the left atrium 140. Typically, the mitral valve has a D-shaped anterior leaflet 110 oriented toward the aortic valve, with a crescent shaped posterior leaflet 115. The leaflets intersect with the atrium 170 at the mitral annulus 190.

In a healthy heart, these muscles and their chords support the mitral and tricuspid valves, allowing the leaflets to resist the high pressure developed during contractions (pumping) of the left and right ventricles. In a healthy heart, the chords become taut, preventing the leaflets from being forced into the left or right atria and everted. Prolapse is a term used to describe the condition wherein the coaptation edges of each leaflet initially may coapt and close, but then the leaflets rise higher and the edges separate and the valve leaks. This is normally prevented by contraction of the papillary muscles and the normal length of the chords. Contraction of the papillary muscles is simultaneous with the contraction of the ventricle and serves to keep healthy valve leaflets tightly shut at peak contraction pressures exerted by the ventricle.

II. Characteristics and Causes of Mitral Valve Dysfunction

Valve malfunction can result from the chords becoming stretched, and in some cases tearing. When a chord tears, the result is a flailed leaflet. Also, a normally structured valve may not function properly because of an enlargement of the valve annulus pulling the leaflets apart. This condition is referred to as a dilation of the annulus and generally results from heart muscle failure. In addition, the valve may be defective at birth or because of an acquired disease, usually infectious or inflammatory.

FIG. 5 shows a cutaway view of a human heart 200 with a prolapsed mitral valve. The prolapsed valve does not form a tight seal during ventricular systole, and thus allows blood to be regurgitated back into the left atrium during ventricular contraction. The anterior 220 and posterior 225 leaflets are shown rising higher than normal (i.e., prolapsing) into the left atrium. The arrows indicate the direction of regurgitant flow. Among other causes, regurgitation can result from redundant valve leaflet tissue or from stretched chords 210 that are too long to prevent the leaflets from being blown into the atrium. As a result, the leaflets do not form a tight seal, and blood is regurgitated into the atrium.

FIG. 6 shows a cutaway view of a human heart 300 with a flailing mitral valve 320. The flailing valve also does not form a tight seal during ventricular systole. Blood thus regurgitates back into the left atrium during ventricular contraction, as indicated by the arrows. Among other causes, regurgitation can also result from torn chords 310. As an example, FIG. 7 shows a cutaway view of a human heart where the anterior leaflet 910 has torn chords 920. As a result, valve flailing and blood regurgitation occur during ventricular systole.

As a result of regurgitation, "extra" blood back flows into the left atrium. During subsequent ventricular diastole (when the heart relaxes), this "extra" blood returns to the left ventricle, creating a volume overload, i.e., too much blood in the left ventricle. During subsequent ventricular systole (when the heart contracts), there is more blood in the ventricle than expected. This means that: (1) the heart must pump harder to move the extra blood; (2) too little blood may move from the heart to the rest of the body; and (3) over time, the left ventricle may begin to stretch and enlarge to accommodate the larger volume of blood, and the left ventricle may become weaker.

Although mild cases of mitral valve regurgitation result in few problems, more severe and chronic cases eventually weaken the heart and can result in heart failure. Mitral valve regurgitation can be an acute or chronic condition. It is sometimes called mitral insufficiency.

III. Prior Treatment Modalities

In the treatment of mitral valve regurgitation, diuretics and/or vasodilators can be used to help reduce the amount of blood flowing back into the left atrium. An intra-aortic balloon counterpulsation device is used if the condition is not stabilized with medications. For chronic or acute mitral valve regurgitation, surgery to repair or replace the mitral valve is often necessary.

To date, invasive, open heart surgical approaches have been used to repair or replace the mitral valve with either a mechanical valve or biological tissue (bioprosthetic) taken from pigs, cows, or horses.

The need remains for simple, cost-effective, and less invasive devices, systems, and methods for treating dysfunction of a heart valve, e.g., in the treatment of mitral valve regurgitation.

SUMMARY OF THE INVENTION

The invention provides devices, systems and methods that supplement, repair, or replace a native heart valve leaflet. The devices, systems, and methods include an implant that, in use, rests adjacent a valve annulus. The implant defines a pseudo-annulus. The implant includes a neoleaflet element that occupies the space of at least a portion of one native valve leaflet. The implant allows the native leaflets to coexist with the implant, or if desired or indicated, one or more native leaflets can be removed and replaced by the implant. The neoleaflet element of the implant is shaped and compressed to mimic the one-way valve function of a native leaflet. The implant includes spaced-apart struts that are sized and configured to contact tissue near or within the heart valve annulus to brace the implant against migration within the annulus during the one-way valve function.

Other features and advantages of the invention shall be apparent based upon the accompanying description, drawings, and claims.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

Figure 1:
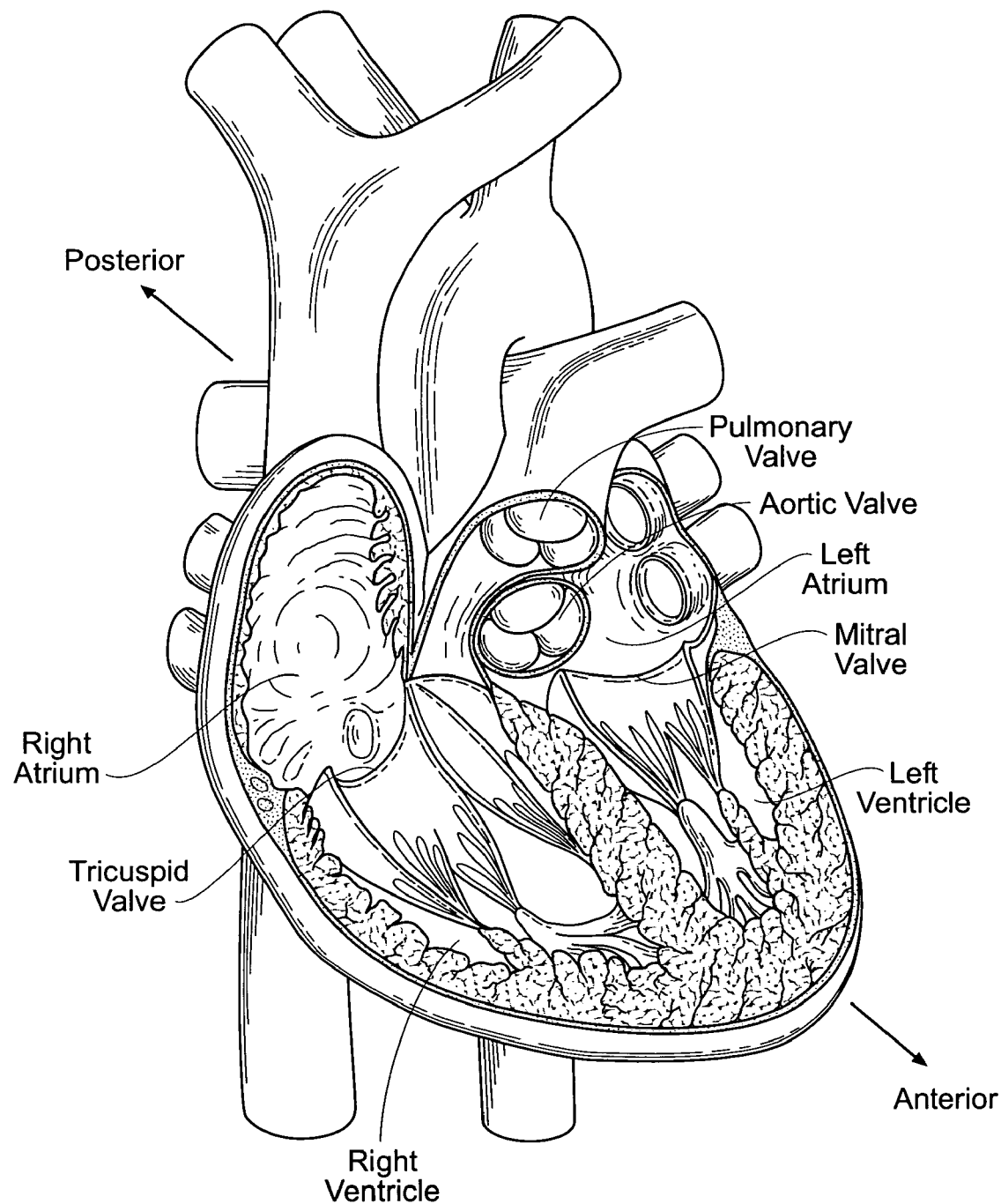
FIG. 1 is a perspective, anterior anatomic view of the interior of a healthy heart.
Figure 2:
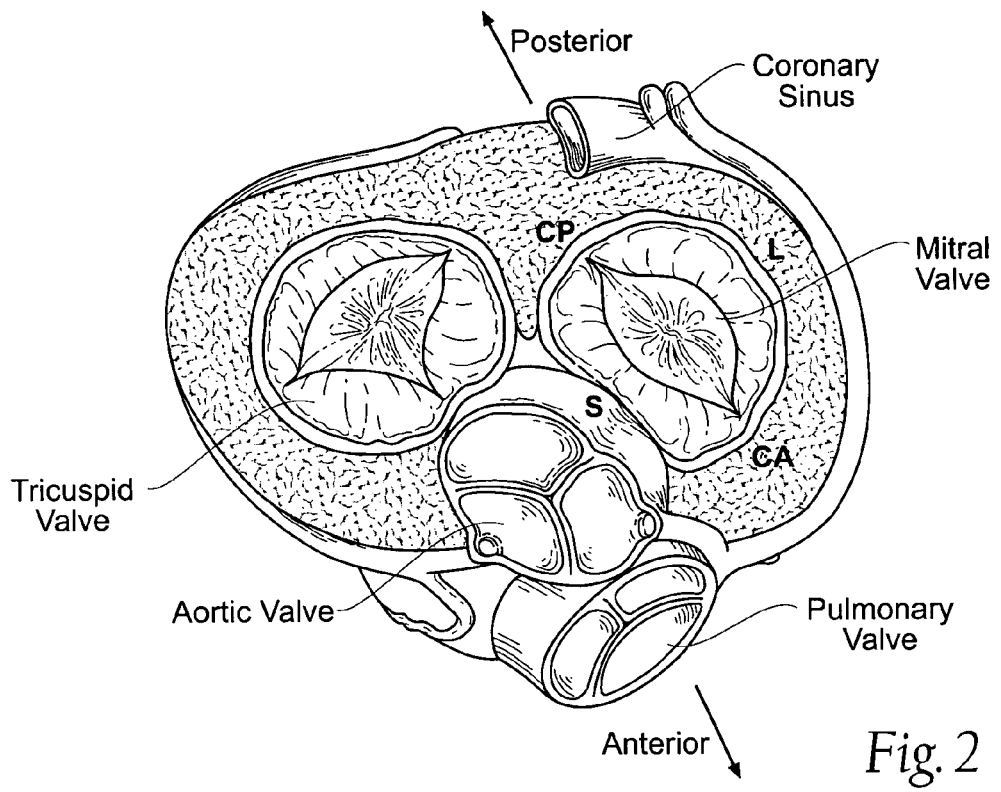
FIG. 2 is a superior anatomic view of the interior of a healthy heart, with the atria removed, showing the condition of the heart valves during ventricular diastole.
Figure 3:
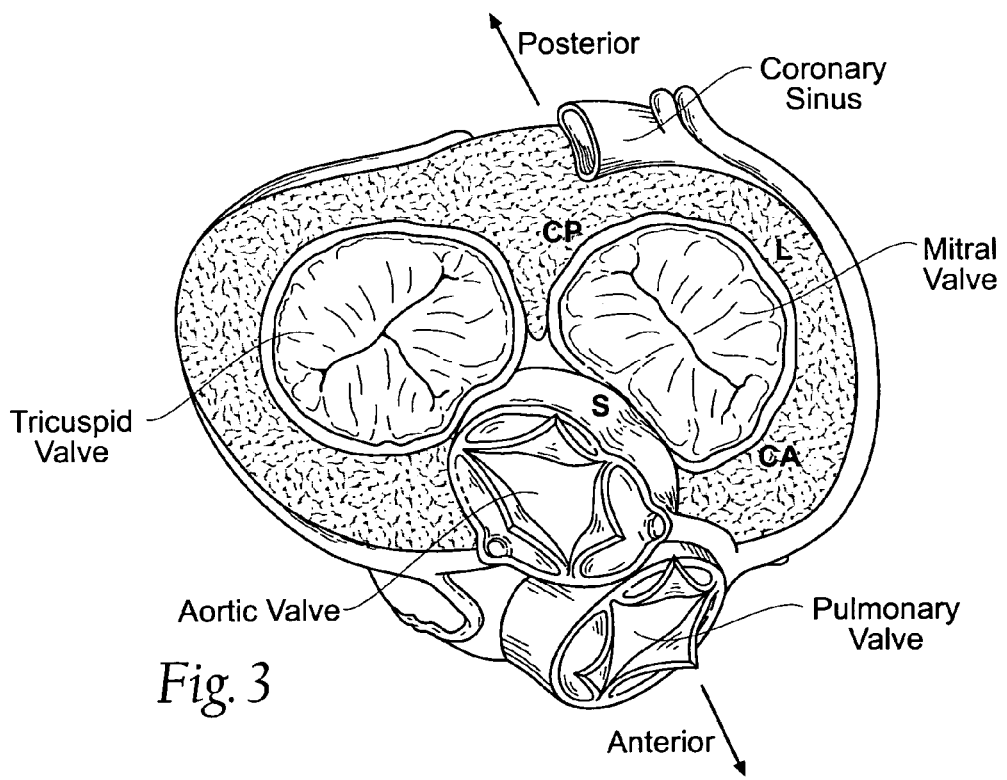
FIG. 3 is a superior anatomic view of the interior of a healthy heart, with the atria removed, showing the condition of the heart valves during ventricular systole.
Figure 4:
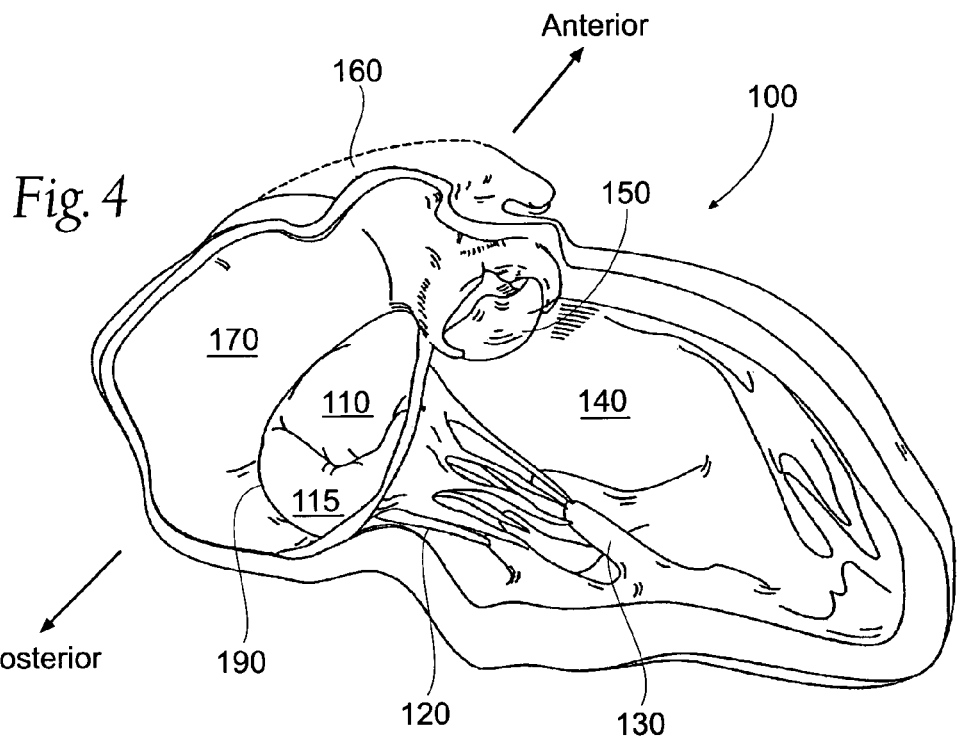
FIG. 4 is a posterior oblique cutaway view of a portion of a human heart, showing a healthy mitral valve during ventricular systole, with the leaflets properly coapting.
Figure 5:
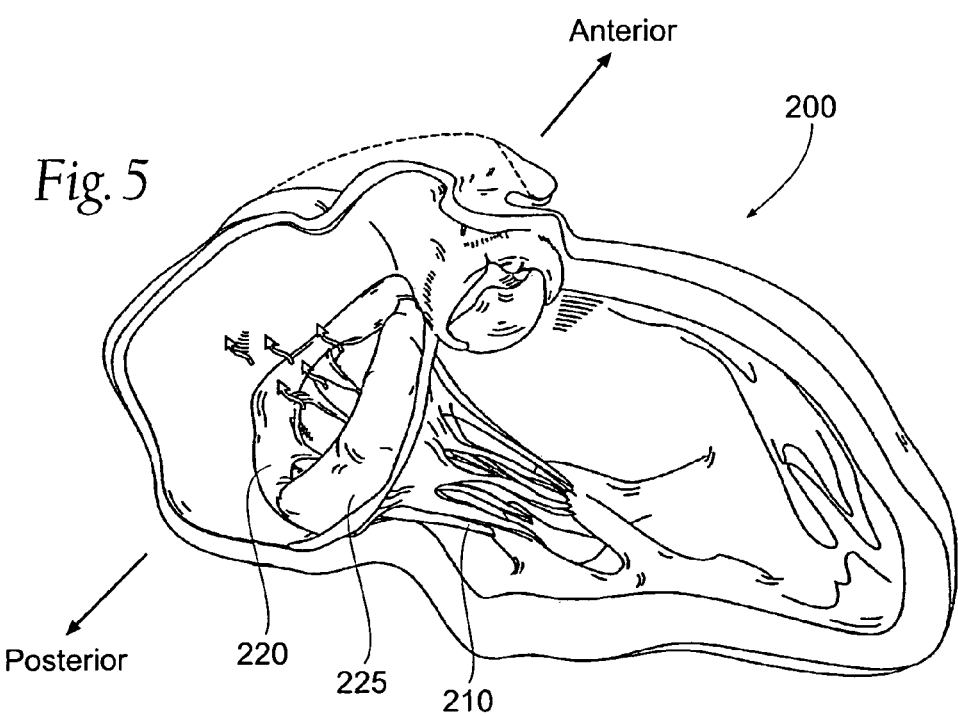
FIG. 5 is a posterior oblique cutaway view of a portion of a human heart, showing a dysfunctional prolapsing mitral valve during ventricular systole, with the leaflets not properly coapting, causing regurgitation.
Figure 6:
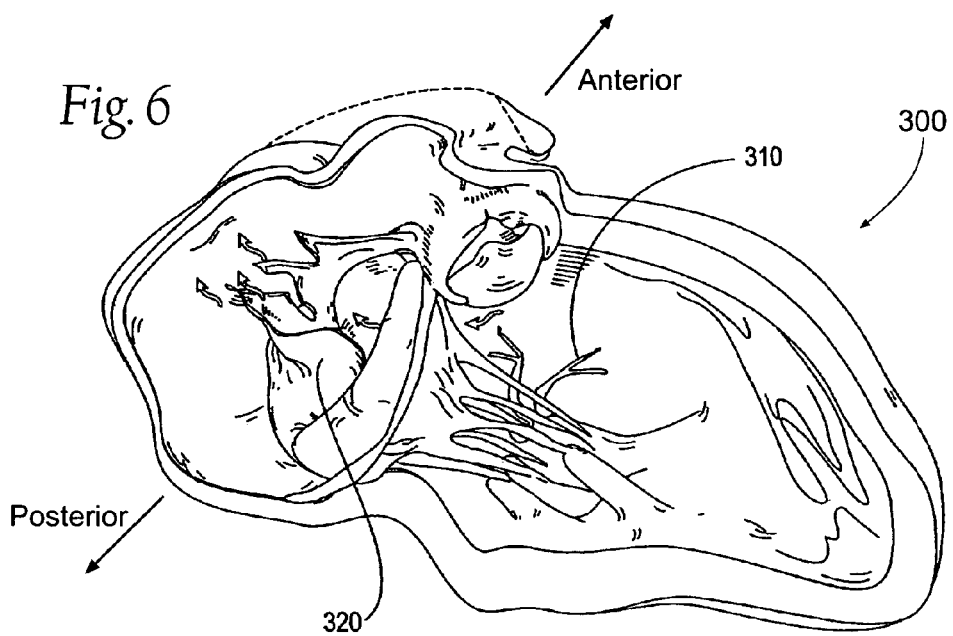
FIG. 6 is a posterior oblique cutaway view of a portion of a human heart, showing a dysfunctional mitral valve during ventricular systole, with the leaflets flailing, causing regurgitation.
Figure 7:
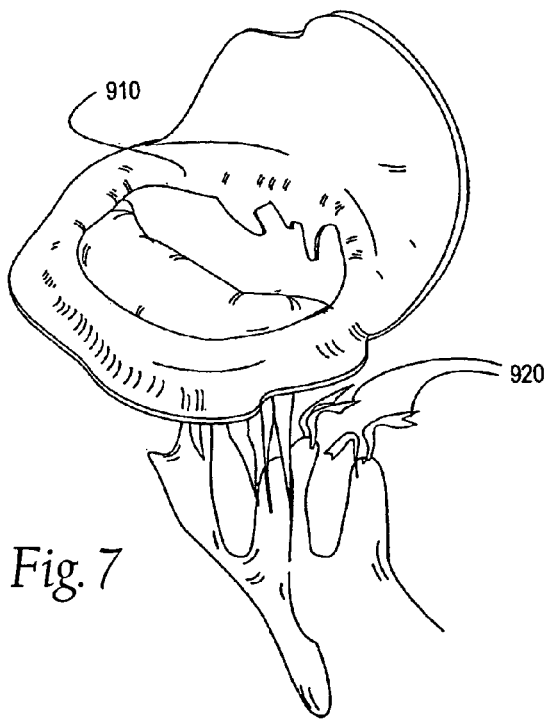
FIG. 7 is a posterior oblique cutaway view of a portion of a human heart, showing a dysfunctional mitral valve during ventricular systole, caused by torn chords, that leads to regurgitation.
Figure 8:
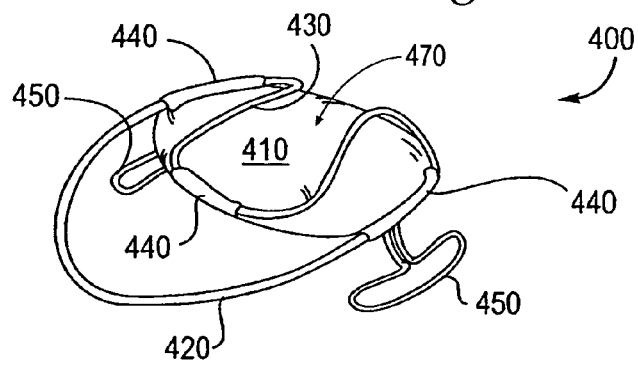
FIG. 8 is a perspective view of an implant that supplements, repairs, or replaces a native heart valve leaflet, the implant being sized and configured to extend about a heart valve annulus and including a neoleaflet element that occupies the space of at least one native valve leaflet.

FIGS. 8 and 9 show an implant 400 sized and configured to supplement, repair, or replace a dysfunctional native heart valve leaflet or leaflets. In use (see, in particular, FIG. 9), the implant 400 defines a pseudo-annulus that rests adjacent the native valve annulus and includes a neoleaflet element that occupies the space of at least a portion of one native valve leaflet. The implant 400 allows the native leaflets to coexist with the implant 400. If desired or indicated, one or more native leaflets can be removed and replaced by the implant 400.

In its most basic form, the implant 400 is made—e.g., by machining, bending, shaping, joining, molding, or extrusion—from a biocompatible metallic or polymer material, or a metallic or polymer material that is suitably coated, impregnated, or otherwise treated with a material to impart biocompatibility, or a combination of such materials. The material is also desirably radio-opaque to facilitate fluoroscopic visualization.

As FIG. 8 shows, the implant 400 includes a base or scaffold 420 that, in the illustrated embodiment, is sized and configured to rest adjacent the mitral annulus. At least a portion of the base 420 forms an annular body that approximates the shape of the native annulus. For this reason, the base 420 will also be referred to as a "pseudo-annulus."

Figure 9A:
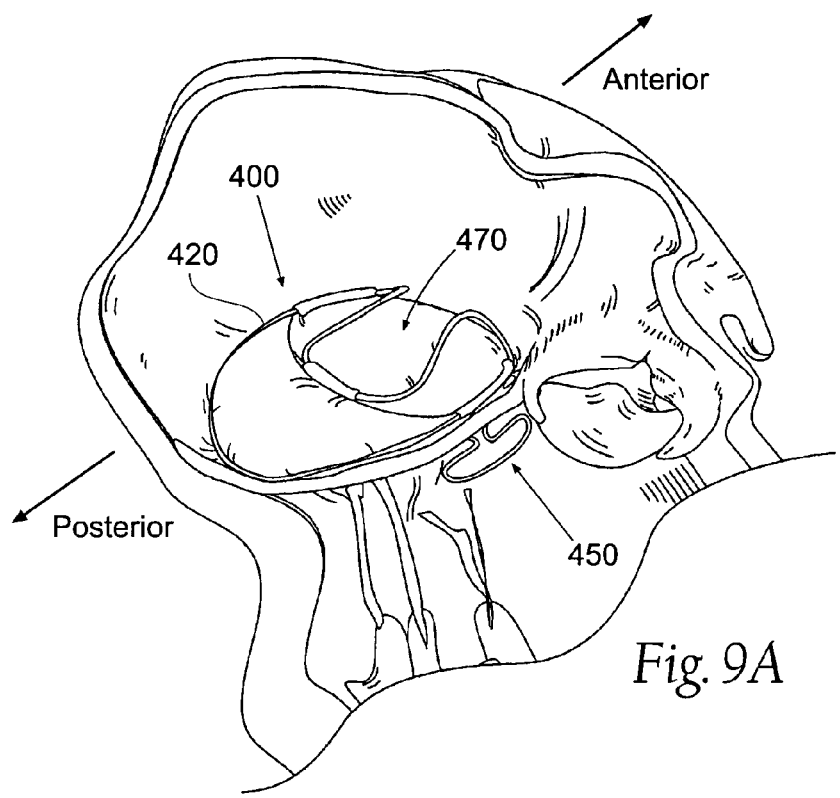
FIG. 9A is a perspective, anatomic view of the implant shown in FIG. 8, with the neoleaflet element installed over an anterior leaflet of a mitral valve to restore normal function.
Figure 9B:
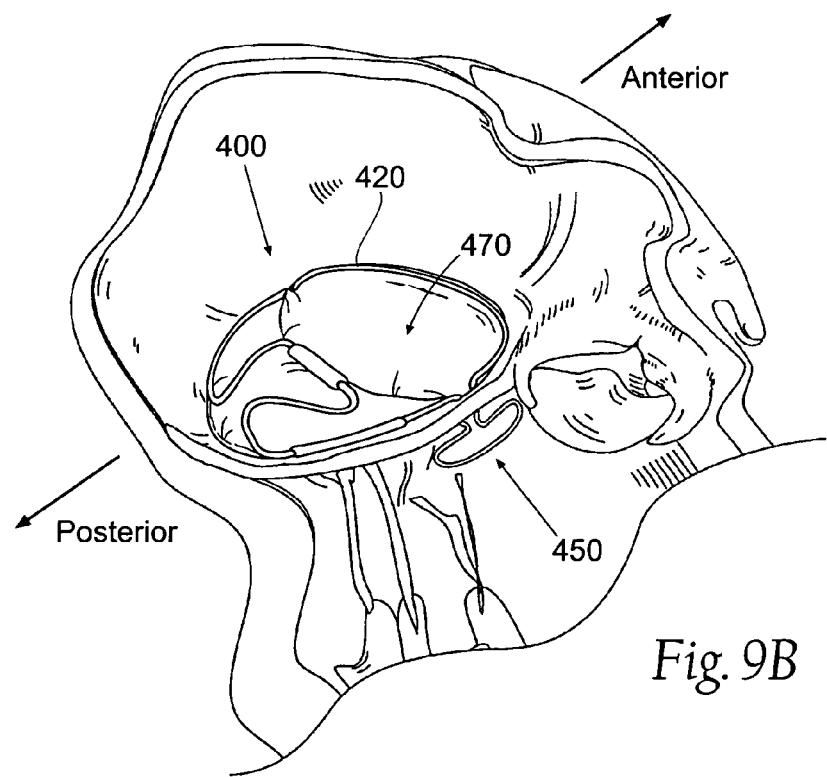
FIG. 9B is a perspective, anatomic view of the implant of the type shown in FIG. 8, with the neoleaflet element installed over a posterior leaflet of a mitral valve to restore normal function to the native valve leaflet.

The base 420 supports a bridge 430 that extends into the valve. The bridge 430 is sized and configured (see FIG. 9A) to overlay the space of at least a portion of one native valve leaflet. In FIG. 9A, the bridge 430 overlays an anterior leaflet. However, as FIG. 9B shows, the bridge 430 could be oriented to overlay a posterior leaflet. As will be described later (see FIG. 11), two bridges can be formed to overlay both leaflets.

As FIG. 8 shows, the implant 400 includes a material 410 that covers or spans the bridge 430. The spanning material 410 may be attached to the implant 400 with one or more attachment means 440. For example, the spanning materials 410 may be sewn, glued, or welded to the implant 400, or it may be attached to itself when wrapped around the implant 400. The spanning material 410 may be made from a synthetic material (for example, thin Nitinol, polyester fabric, polytetrafluoroethylene or PTFE, silicone, or polyurethane) or a biological material (for example, human or animal pericardium).

Together, the bridge 430 and the spanning material 410 comprise a neoleaflet element 470 coupled to the base 420. The neoleaflet element 470 may be rigid, semi-rigid, or flexible. The neoleaflet element 470 is coupled to the base 420 in a manner that exerts a mechanical, one-way force to provide a valve function that responds to differential pressure conditions across the neoleaflet element. In response to one prescribed differential pressure condition, the neoleaflet element 470 will deflect and, with a native leaflet, assume a valve opened condition. In response to another prescribed pressure condition, the neoleaflet element 470 will resist deflection and, by coaptation with a native leaflet (or a companion neoleaflet element) at, above, or below the annulus plane, maintain a valve closed condition.

In the context of the illustrated embodiment (when installed in a mitral valve annulus), the neoleaflet element resists being moved in the cranial (superior) direction (into the atrium), when the pressure in the ventricle exceeds the pressure in the atrium—as it would during ventricular systole. The neoleaflet element 470 may move, however, in the caudal (inferior) direction (into the ventricle), when the pressure in the ventricle is less than the pressure in the atrium—as it would during ventricular diastole. The neoleaflet element 470 thereby mimics the one-way valve function of a native leaflet, to prevent retrograde flow.

The implant 400 is sized and shaped so that, in use adjacent the valve annulus of the mitral valve, it keeps the native valve leaflet closed during ventricular systole (as shown in FIGS. 9A and 9B), to prevent flailing and/or prolapse of the native valve leaflet it overlays during ventricular systole. The implant 400 thus restores to the heart valve leaflet or leaflets a normal resistance to the high pressure developed during ventricular contractions, resisting valve leaflet eversion and/or prolapse and the resulting back flow of blood from the ventricle into the atrium during ventricular systole. The pressure difference serves to keep valve leaflets tightly shut during ventricular systole. The implant 400, however, does not interfere with opening of the native valve leaflet or leaflets during ventricular diastole (see, e.g., FIG. 12). The implant 400 allows the leaflet or leaflets to open during ventricular diastole, so that blood flow occurs from the atrium into the ventricle. The implant 400 thereby restores normal one-way function to the valve, to prevent retrograde flow.

The functional characteristics of the implant 400 just described can be imparted to the neoleaflet element 470 in various ways. For example, hinges and springs (mechanical or plastic) can be used to couple the bridge to the base. Desirably, the implant 400 is made from materials that provide it with spring-like characteristics.

As shown in FIG. 8, in the illustrated embodiment, the base 420 and bridge 430 are shaped from a length of wire-formed material. The shape and material properties of the implant determine its physical spring-like characteristics as well as its ability to open in one direction only. The spring-like characteristics of the implant 400 allow it to respond dynamically to changing differential pressure conditions within the heart.

Figure 12:
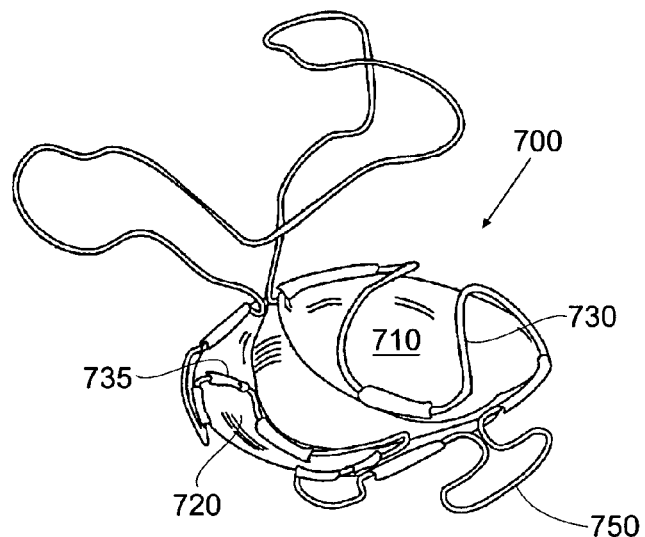
FIG. 12 is a perspective view of the implant shown in FIG. 11, with the two neoleaflet elements in a valve opened condition, as would exist during ventricular diastole.

More particularly, in the illustrated mitral valve embodiment, when greater pressure exists superior to the bridge 430 than inferior to the bridge (i.e., during ventricular diastole), the shape and material properties of the bridge 430 accommodate its deflection into the ventricle—i.e., an opened valve condition (as FIG. 12 shows in another illustrative embodiment). When greater pressure exists inferior to the bridge 430 than superior to the bridge (i.e., during ventricular systole), the shape and material properties of the bridge 430 enable it to resist superior movement of the leaflet into the atrium, and otherwise resist eversion and/or prolapse of the valve leaflet into the atrium (as FIGS. 9A and 9B also show).

The implant 400 may be delivered percutaneously, thoracoscopically through the chest, or using open heart surgical techniques. If delivered percutaneously, the implant 400 may be made from a superelastic material (for example superelastic Nitinol alloy) enabling it to be folded and collapsed such that it can be delivered in a catheter, and will subsequently self-expand into the desired shape and tension when released from the catheter.

Figure 21A:
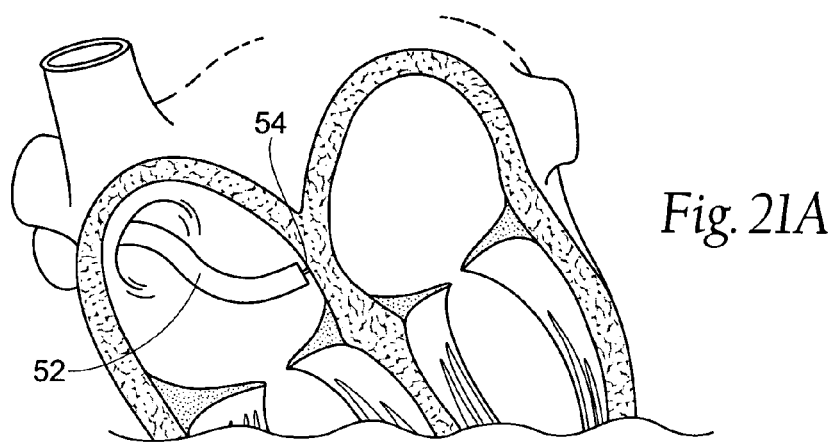
FIGS. 21A to 21C diagrammatically show a method of gaining intravascular access to the left atrium for the purpose of deploying a delivery catheter to place an implant in a valve annulus to supplement, repair, or replace a native heart valve leaflet.
Figure 21B:
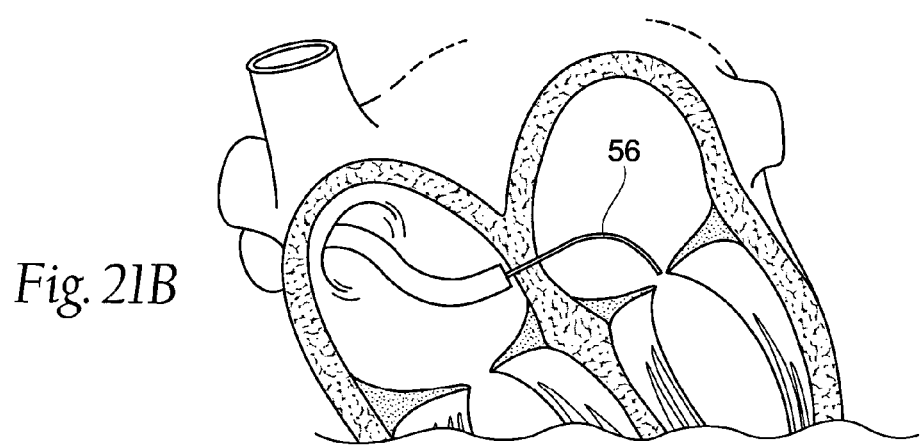
Figure 21C:
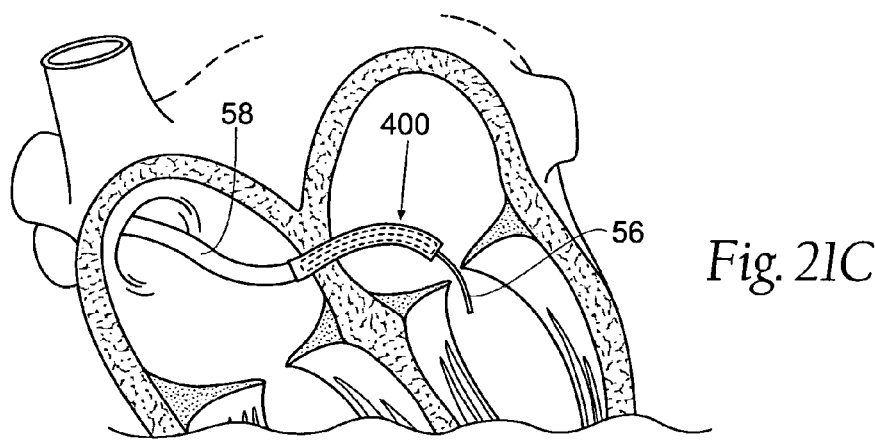

For example, percutaneous vascular access can be achieved by conventional methods into the femoral or jugular vein. As FIG. 21A shows, under image guidance (e.g., fluoroscopic, ultrasonic, magnetic resonance, computed tomography, or combinations thereof), a catheter 52 is steered through the vasculature into the right atrium. A needle cannula 54 carried on the distal end of the catheter is deployed to pierce the septum between the right and left atrium. As FIG. 21B shows, a guide wire 56 is advanced trans-septally through the needle catheter 52 into the left atrium. The first catheter 52 is withdrawn, and (as FIG. 21C shows) under image guidance, an implant delivery catheter 58 is advanced over the guide wire 56 into the left atrium into proximity with the mitral valve. Alternatively, the implant delivery catheter 58 can be deployed trans-septally by means of surgical access through the right atrium.

The distal end of the catheter 58 encloses an implant 400, like that shown in FIG. 8, which is constrained in a collapsed condition. A flexible push rod in the catheter 58 can be used to expel the implant 400 from the catheter 58. Free of the catheter, the implant 400 will self-expand to its preordained configuration, e.g., like that shown in FIGS. 9A or 9B.

The implant 400 may be fixed to the annulus in various ways. For example, the implant 400 may be secured to the annulus with sutures or other attachment means (i.e. barbs, hooks, staples, etc.) Also, the implant 400 may be secured with struts or tabs 450 (see FIGS. 8 and 9A), that extend from the base 420 above or below the plane of the annulus. The struts 450 are preferably configured with narrow connecting members that extend through the valve orifice so that they will not interfere with the opening and closing of the valve.

In this arrangement, the struts 450 are desirably sized and configured to contact tissue near or within the heart valve annulus to brace the base 420 against migration within the annulus during the one-way valve function of the neoleaflet element. In this arrangement, it is also desirable that the base 420 be "elastic," i.e., the material of the base 420 is selected to possess a desired spring constant. This means that the base 420 is sized and configured to possess a normal, unloaded, shape or condition (shown in FIG. 8), in which the base 420 is not in net compression, and the struts 450 are spaced apart farther than the longest cross-annulus distance between the tissue that the struts 450 are intended to contact. In the illustrated embodiment, the base 420 is shown resting along the major (i.e., longest) axis of the valve annulus, with the struts 450 contacting tissue at or near the leaflet commissures. However, other orientations are possible. The struts 450 need not rest at or near the leaflet commissures, but may be significantly removed from the commissures, so as to gain padding from the leaflets. The spring constant imparts to the base 420 the ability to be elastically compressed out of its normal, unloaded condition, in response to external compression forces applied at the struts 450. The base 420 is sized and configured to assume an elastically loaded, in net compression condition, during which the struts 450 are spaced apart a sufficiently shorter distance to rest in engagement with tissue at or near the leaflet commissures (or wherever tissue contact with the struts 450 is intended to occur) (see FIGS. 9A or 9B). When in its elastically loaded, net compressed condition (see FIGS. 9A and 9B), the base 450 can exert forces to the tissues through the struts 450. These forces hold the base 420 against migration within the annulus. Furthermore, when the struts 450 are positioned at or near the commissures, they tend to outwardly displace tissue and separate tissue along the major axis of the annulus, which also typically stretches the leaflet commissures, shortens the minor axis, and/or reshapes surrounding anatomic structures. The base 450 can also thereby reshape the valve annulus toward a shape more conducive to leaflet coaptation. It should be appreciated that, in order to be therapeutic, the implant may only need to reshape the annulus during a portion of the heart cycle, such as during ventricular systolic contraction. For example, the implant may be sized to produce small or negligible outward displacement of tissue during ventricular diastole when the tissue is relaxed, but restrict the inward movement of tissue during ventricular systolic contraction.

As the preceding disclosure demonstrates, different forms of heart valve treatment can be performed using a single implant.

Implants having one or more of the technical features just described, to thereby function in situ as a neo-leaflet, may be sized and configured in various ways. Various illustrative embodiments will now be described.

Figure 10:
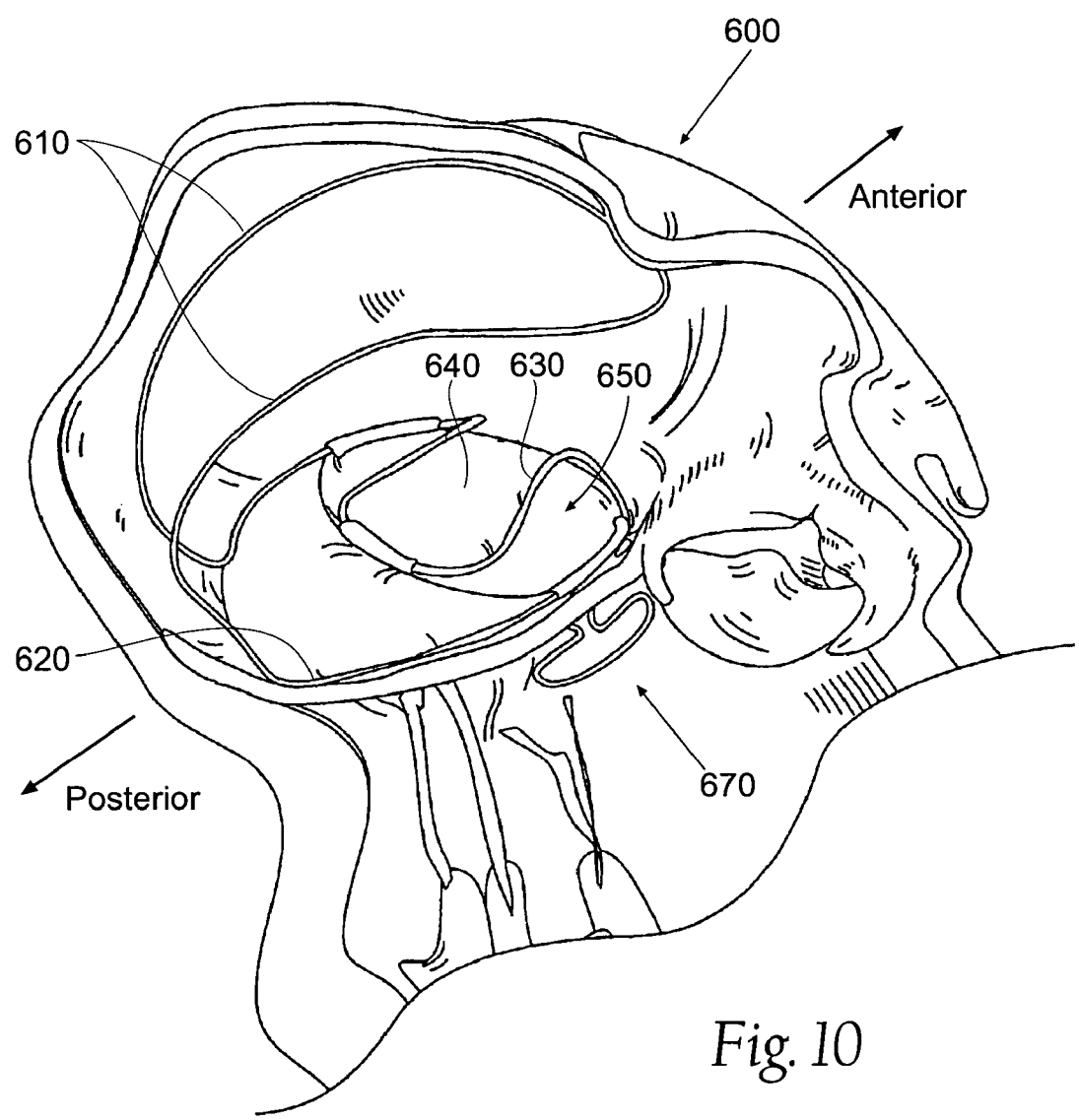
FIG. 10 is a perspective view of another illustrative embodiment of an implant that supplements, repairs, or replaces a native heart valve leaflet, the implant being shown installed on a mitral valve annulus and having a neoleaflet element that occupies the space of at least one native valve leaflet, the implant also including a framework that rises above the neoleaflet element in the atrium to help fix and stabilize the implant.

In FIG. 10, an implant 600 (like implant 400) includes a base 620 that defines a pseudo-annulus, with a bridge 630 carrying a spanning material 640 together comprising a neoleaflet element 650 appended to the base 620 within the pseudo-annulus. The neoleaflet element 650 overlays an anterior native leaflet with the same purpose and function described for the implant 400. Alternatively, the neoleaflet element 650 could overlay a posterior native leaflet, as FIG. 9B shows. The implant 600 also includes struts 670, which desirably contact and exert force against tissue near or within the annulus (in the manner previously described) to brace the base 420 against migration within the annulus.

In addition, the implant 600 includes an orientation and stabilization framework 610 that may extend from the annulus to the atrial dome. In FIG. 10, the framework 610 rises from the base 620 with two substantially parallel arched wires, which connect to form a semicircular hoop above the base 620. The framework 610 helps to accurately position the implant 600 within the atrium, and also helps to secure the implant 600 within the atrium.

Preferably the framework 610 does not interfere with atrial contractions, but instead is compliant enough to contract with the atrium. As such, the implant 600 may have nonuniform flexibility to improve its function within the heart.

Figure 11:
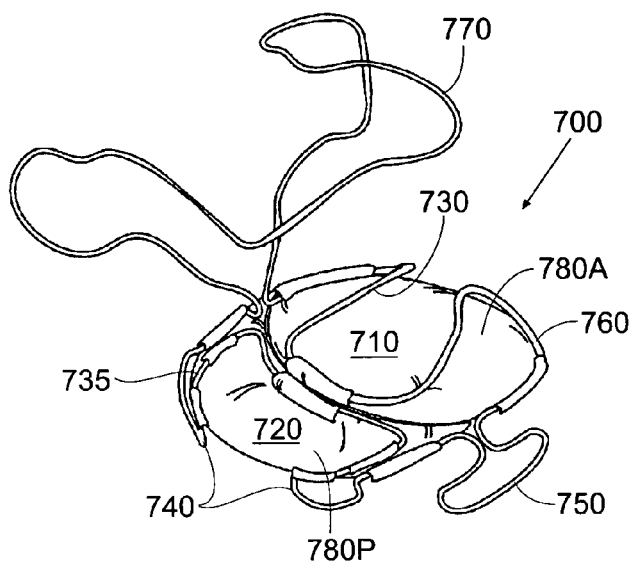
FIG. 11 is a perspective view of another illustrative embodiment of an implant that supplements, repairs, or replaces a native heart valve leaflet, the implant being sized and configured to extend about a heart valve annulus and including two neoleaflet elements that occupy the space of two native valve leaflets.

FIGS. 11 and 12 show another illustrative embodiment of an implant 700. In FIGS. 11 and 12, the implant 700 contains two neo-leaflet elements. The implant 700 includes an anterior bridge 730 spanned by an anterior bridge material 710, and a posterior bridge 735 spanned by a posterior bridge material 720. The bridges and materials together comprise anterior and posterior neoleaflet elements 780A and 780P. The implant 700 also includes an orientation and stabilization framework 770, shown having a configuration different than the framework 610 in FIG. 9, but having the same function and serving the same purpose as previously described for the framework 610.

In FIGS. 11 and 12, the base 760 includes structures like the anchoring clips 740 that, in use, protrude above the plane formed by the annulus of the valve. Additionally, the implant 700 may be secured with struts 750 that extend from the base 760 on narrow connecting members and below the plane of the annulus into the ventricular chamber. The anchoring clips 740 and struts 750 desirably contact and exert force against tissue near or within the annulus (in the manner previously described) to brace the base 760 against migration within the annulus. FIG. 11 shows the dual neo-S leaflets 780A and 780B (i.e., the covered anterior and posterior bridges 730 and 735) in a closed valve position. FIG. 12 shows the dual neo-leaflets 780A and 780B in an open valve position.

Figure 13:
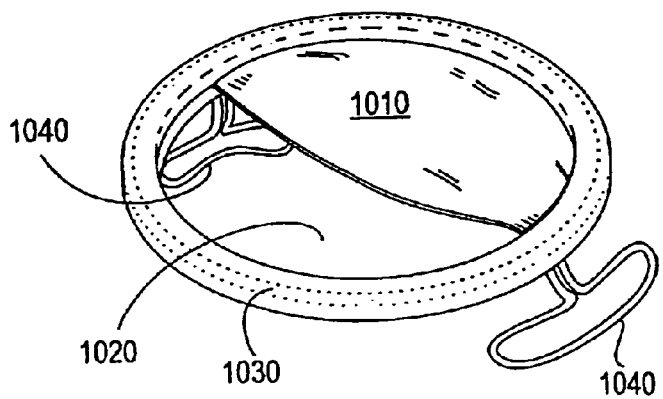
FIG. 13 is a perspective view of another illustrative embodiment of an implant that supplements, repairs, or replaces a native heart valve leaflet, the implant being sized and configured to extend about a heart valve annulus and including a neoleaflet element formed by a membrane.

FIG. 13 shows another illustrative embodiment of an implant 1000 having a full sewing ring 1030 with a membrane 1010 that serves as a neo-leaflet. The device 1000 has an opening 1020 though the sewing ring 1030 opposite the membrane 1010 for blood flow. Alternatively, this embodiment could have two neo-leaflets. This embodiment could be surgically attached to the valve annulus and/or combined with a framework for anchoring the device within the atrium using catheter based intraluminal techniques. Additionally, the device may be secured with struts 1040 that extend from the base on narrow connecting members and below the plane of the annulus into the ventricular chamber. The struts 1040, which desirably contact and exert force against tissue near or within the annulus (in the manner previously described) to brace the base 420 against migration within the annulus.

As can be seen, a given implant may carry various structures or mechanisms to enhance the anchorage and stabilization of the implant in the heart valve annulus. The mechanisms may be located below the plane of the annulus, to engage infra-annular heart tissue adjoining the annulus in the ventricle, and/or be located at or above the plane of the annulus, to engage tissue on the annulus or in the atrium. These mechanisms increase the surface area of contact between the implant and tissue. A given implant can also include tissue in-growth surfaces, to provide an environment that encourages the in-growth of neighboring tissue on the implant. Once in-growth occurs, the implant becomes resistant to migration or dislodgment from the annulus. Conventional in-growth materials such as polyester fabric can be used.

Figure 14:
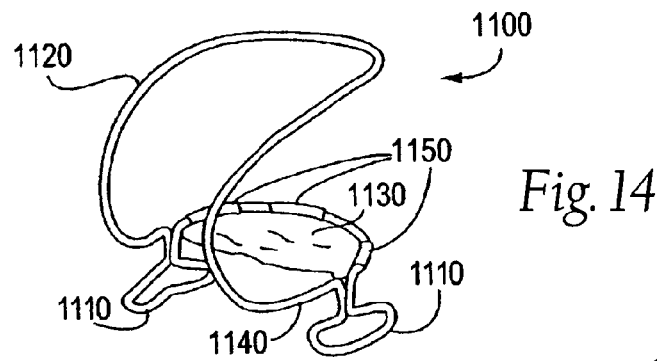
FIG. 14 is a perspective view of another illustrative embodiment of an implant that supplements, repairs, or replaces a native heart valve leaflet, the implant being sized and configured to extend about a heart valve annulus and including a neoleaflet element formed by a membrane, the implant also including a framework that rises above the neoleaflet element in the atrium to help fix and stabilize the implant.

FIG. 14 shows another illustrative embodiment of an implant 1100 having a framework 1120 and struts or tabs 1110. This implant 1100 includes a membrane 1130, that serves as a neo-leaflet, attached to the base 1140 of the device with an attachment means 1150.

Figure 15:
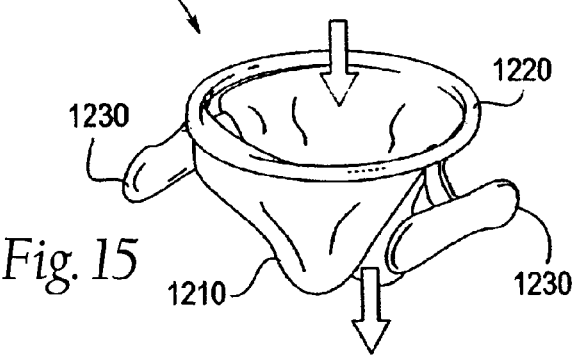
FIG. 15 is a perspective view of another illustrative embodiment of an implant that supplements, repairs, or replaces a native heart valve leaflet, the implant being sized and configured to extend about a heart valve annulus and including two neoleaflet elements to form a duckbill valve, the valve being shown in an opened condition as would exist during ventricular diastole.

FIG. 15 shows another illustrative embodiment of an implant 1200. In this embodiment, the implant 1200 includes a base 1220 that defines a pseudo-annulus and that, in use, is rests adjacent all or a portion of a native valve annulus. The base 1240 supports a duckbill valve 1210, which forms a neoleaflet element. Peripherally supported on the base 1240, the duckbill valve 1210 rests in the pseudo-annulus. Struts 1230 (which also carry additional tab structures to increase the surface area of tissue contact) help brace the base 1240 to tissue near or within the heart valve annulus.

Figure 16:
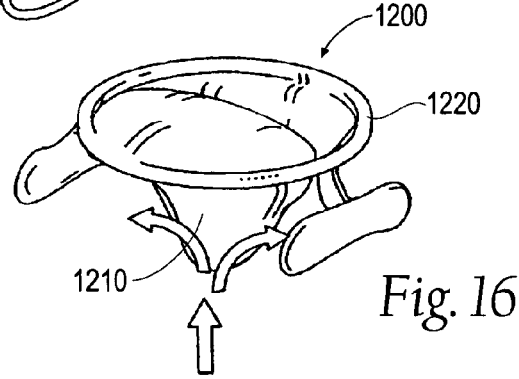
FIG. 16 is a perspective view of the implant shown in FIG. 15, the duckbill valve being shown in a closed condition as would exist during ventricular systole.

In this embodiment, the duckbill valve 1210 replaces the native anterior and posterior leaflets. The duckbill valve 1210 serves as dual neo-leaflets, which mutually open and close in response to changes in pressure, replacing the function of the native leaflets. FIG. 15 shows the duckbill valve 1210 in the open valve position. In FIG. 15, the arrow shows the direction of blood flow through the opened valve. FIG. 16 shows the duckbill valve in the closed valve position. When closed, the duckbill valve 1210 resists eversion and regurgitation.

Figure 17:
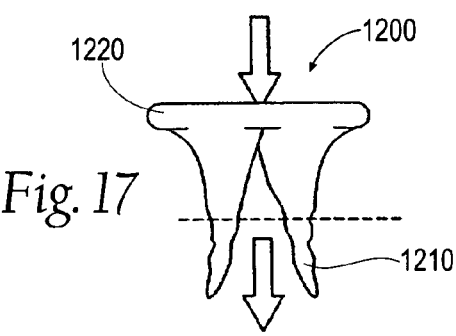
FIGS. 17 and 18 are side views of the implant shown, respectively, in FIGS. 15 and 16, with the duckbill valve, respectively, in an opened and a closed condition.
Figure 18:
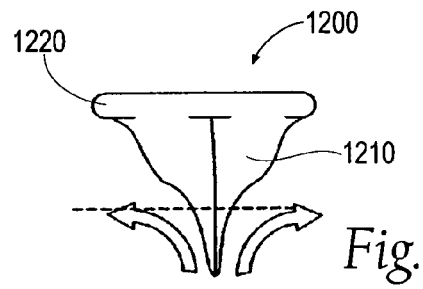

When the implant 1200 is used to replace a mitral valve (see FIGS. 17 and 18), the duckbill valve 1210 extends from the plane of the valve annulus and into the ventricle. The duckbill valve 1210 is shown to have a more rigid or thick composition emerging from the base member, and gradually becoming less rigid or thick away from the base member. This variation in mechanical properties ensures a valve that responds dynamically to pressure changes, but that is also rigid enough to not become everted. FIG. 17 shows the valve 1210 in an opened valve condition. In FIG. 17, the arrow shows the direction of blood flow through the opened valve. FIG. 18 shows the duckbill valve in the closed valve position, without eversion and regurgitation.

Figure 19:
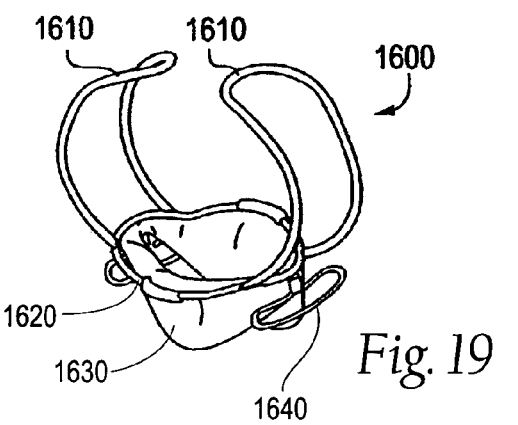
FIG. 19 is a perspective view of another illustrative embodiment of an implant that supplements, repairs, or replaces a native heart valve leaflet, the implant being sized and configured to extend about a heart valve annulus and including two neoleaflet elements formed by a duckbill valve, the valve being shown in an opened condition as would exist during ventricular diastole, the implant also including a framework that rises above the neoleaflet elements in the atrium to help fix and stabilize the implant.
Figure 20:
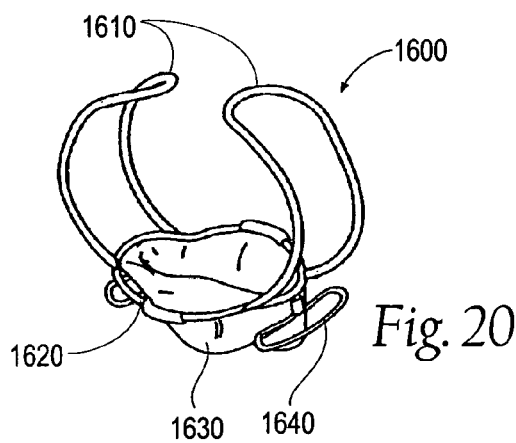
FIG. 20 is a perspective view of the implant shown in FIG. 19, the duckbill valve being shown in a closed condition as would exist during ventricular systole.

FIGS. 19 and 20 show another illustrative embodiment of an implant 1600 of the type shown in FIGS. 15 and 16. Like the implant 1200, the implant 1600 includes base 1620 defining a pseudo-annulus to which a duckbill valve 1630 is appended, which serves as a neoleaflet element to replace the native anterior and posterior leaflets and serves as dual neo-leaflets. FIG. 19 shows the duckbill valve 1630 in the open valve position, allowing forward flow of blood through the opened valve. FIG. 20 shows the duckbill valve 1630 in the closed valve position, resisting eversion and regurgitation.

In FIGS. 19 and 20, the implant 1600 includes an orientation and stabilization framework 1610. The framework 1610 rises from the base 1620 as two arches extending from opposite sides of the base 1620. The dual arch framework 1610 possesses compliance to contract with the atrium. As before explained, the framework 1610 helps to accurately position the implant 1600 within the atrium, and also helps to secure the implant 600 within the atrium. The implant 1600 also includes struts 1640, which desirably contact and exert force against tissue near or within the annulus (in the manner previously described) to brace the base 1620 against migration within the annulus.

While the new devices and methods have been more specifically described in the context of the treatment of a mitral heart valve, it should be understood that other heart valve types can be treated in the same or equivalent fashion. By way of example, and not by limitation, the present systems and methods could be used to prevent or resist retrograde flow in any heart valve annulus, including the tricuspid valve, the pulmonary valve, or the aortic valve. In addition, other embodiments and uses of the invention will be apparent to those skilled in the art from consideration of the specification and practice of the invention disclosed herein. The specification and examples should be considered exemplary and merely descriptive of key technical features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

What is claimed is:

1. A method for supplementing, repairing, or replacing a native heart valve leaflet or leaflets comprising selecting a native heart valve having an annulus, native heart valve leaflets, and generally opposite leaflet commissures spaced apart by a maximum cross-annulus distance defining a major axis of the annulus, providing an implant comprising an elastic scaffold, at least a portion of the elastic scaffold defining a pseudo-annulus, the elastic scaffold comprising a normal, unloaded condition including a spring constant to undergo compression in response to applied external compression forces into an elastically loaded condition, the implant further comprising at least two struts coupled to the elastic scaffold in generally oppositely spaced apart positions defining, when the elastic scaffold is in the normal, unloaded condition, a normal cross-strut distance that is greater than the maximum cross-annulus distance, the implant further comprising a neoleaflet element coupled to the elastic scaffold within pseudo-annulus and being sized and shaped to occupy the space of at least a portion of one native heart valve leaflet to provide a one-way valve function that, in response to a first pressure condition, assumes a valve opened condition within the pseudo-annulus and, in response to a second pressure condition, assumes a valve closed condition within the pseudo-annulus, introducing the implant into a heart with the elastic scaffold in the normal, unloaded condition, applying external compression forces at the at least two struts to reduce the normal cross-strut distance to place the elastic scaffold into the elastically loaded condition, while the elastic scaffold is in the elastically loaded condition, placing the struts into engagement with tissue at or near the leaflet commissures to apply tension and outwardly displace and separate tissue along the major axis of the annulus to reshape the annulus for leaflet coaptation, and while the struts are placed in engagement with tissue at or near the leaftlet commissures, providing a one-way valve function with the neoleaflet element that, in response to a first pressure condition, assumes the valve opened condition and, in response to second pressure condition, assumes the valve closed condition, the at least two struts engaging tissue at or near the leaflet commissures to brace the elastic scaffold while in the elastically loaded condition against migration within the annulus during the one-way valve function.

2. A method according to claim 1 wherein the introducing comprises using an open heart surgical procedure.

3. A method according to claim 1 wherein the introducing comprises using a surgical procedure in which the implant is carried within a catheter.

4. A method according to claim 1 wherein the introducing comprises using an intravascular surgical procedure.

* * * * *